(12) United States Patent
Brazel et al.

(10) Patent No.: US 12,162,072 B2
(45) Date of Patent: Dec. 10, 2024

(54) SUPPORTS FOR CANTILEVERED ELEMENTS DURING ADDITIVE MANUFACTURING AND METHODS OF FORMING SUCH SUPPORTS

(71) Applicant: Howmedica Osteonics Corp., Mahwah, NJ (US)

(72) Inventors: Emma Brazel, Cork (IE); Anthony Maher, Limerick (IE); Sean Russell, Cahir (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 33 days.

(21) Appl. No.: 17/850,180

(22) Filed: Jun. 27, 2022

(65) Prior Publication Data
US 2022/0410272 A1    Dec. 29, 2022

Related U.S. Application Data

(60) Provisional application No. 63/216,272, filed on Jun. 29, 2021.

(51) Int. Cl.
*B22F 12/20*    (2021.01)
*B22F 10/366*   (2021.01)
(Continued)

(52) U.S. Cl.
CPC ............ *B22F 10/43* (2021.01); *B22F 10/366* (2021.01); *B22F 10/47* (2021.01); *B22F 12/20* (2021.01); *B33Y 10/00* (2014.12); *B33Y 40/00* (2014.12)

(58) Field of Classification Search
CPC .......... B22F 10/43; B22F 10/47; B22F 12/20; B22F 2999/00; B22F 10/28; B22F 2203/11; B33Y 10/00; B33Y 40/00; B33Y 80/00; B33Y 30/00; A61F 2002/30891; A61F 2002/30985; A61F 2/3094; A61F 2/3859;
(Continued)

(56) References Cited

U.S. PATENT DOCUMENTS 8,506,836 B2    8/2013 Szuromi et al.
9,573,225 B2    2/2017 Buller et al.
(Continued)

FOREIGN PATENT DOCUMENTS

EP    3632591 A1    4/2020
GB    2515287 A     12/2014

OTHER PUBLICATIONS

Gibson, I., Rosen, D., Stucker, B., Khorasani, M. (2021), Additive Manufacturing Technologies. Springer, Cham., available online Nov. 11, 2020, https://doi.org/10.1007/978-3-030-56127-7 5 (Year: 2020).*

(Continued)

*Primary Examiner* — Rebecca Janssen
(74) *Attorney, Agent, or Firm* — Lerner David LLP

(57) ABSTRACT

An additively manufactured in-process structure includes, a base, a first cantilever element extending from the base, and a first heat sink adjacent to the first cantilever element and configured for absorbing heat from the first cantilever element during an additive manufacturing process. A gap is formed between the first cantilever element and the first heat sink and the first heat sink is spaced from any rigid substrate underlying and supporting the first heat sink.

20 Claims, 6 Drawing Sheets

(51) Int. Cl.
*B22F 10/43* (2021.01)
*B22F 10/47* (2021.01)
*B33Y 10/00* (2015.01)
*B33Y 40/00* (2020.01)

(58) Field of Classification Search
CPC ....... Y02P 10/25; B29C 64/153; B29C 64/30; B29C 64/40
See application file for complete search history.

(56) References Cited

U.S. PATENT DOCUMENTS

| | | | |
|---|---|---|---|
| 9,767,224 B2 | 9/2017 | Chou et al. | |
| 10,471,695 B2 | 11/2019 | Gold et al. | |
| 10,913,258 B2 | 2/2021 | Doherty et al. | |
| 2016/0243620 A1 | 8/2016 | Butcher | |
| 2017/0136539 A1* | 5/2017 | Chou | B22F 10/47 |
| 2018/0178446 A1 | 6/2018 | Nosenzo et al. | |
| 2018/0193955 A1* | 7/2018 | Karp | B33Y 30/00 |
| 2019/0086154 A1* | 3/2019 | Adriany | B33Y 80/00 |
| 2019/0134750 A1 | 5/2019 | Nauka et al. | |
| 2020/0079028 A1* | 3/2020 | Miller | B22F 10/47 |
| 2020/0100909 A1* | 4/2020 | Lang | B33Y 10/00 |

OTHER PUBLICATIONS

Cheng, et al., A numerical investigation of support structure designs for overhangs in powder bed electron beam additive manufacturing, Journal of Manufacturing Processes, Jan. 2020, pp. 187-195, vol. 49.

Cooper, et al., Contact-Free Support Structures for Part Overhangs in Powder-Bed Metal Additive Manufacturing, May 2016, pp. 1-12.

Huang, et al., Topology optimization of lattice support structures for heat conduction in selective laser melting, The International Journal of Advanced Manufacturing Technology, published online: Jul. 22, 2020, pp. 1841-1851, vol. 109.

Paggi, et al., New support structures for reduced overheating on downfacing regions of direct metal printed parts, Proceedings of the Annual International Solid Freeform Fabrication Symposium, 2019, pp. 1626-1640, University of Texas, Austin, TX, USA.

Extended European Search Report including Written Opinion for Application No. 22181724.0 dated Oct. 5, 2022, pp. 1-8.

* cited by examiner

SUPPORTS FOR CANTILEVERED ELEMENTS DURING ADDITIVE MANUFACTURING AND METHODS OF FORMING SUCH SUPPORTS

CROSS-REFERENCE TO RELATED APPLICATIONS

This application claims the benefit of the filing date of U.S. Provisional Application No. 63/216,272 filed Jun. 29, 2021, the disclosure of which is hereby incorporated by reference in its entirety.

FIELD

The present disclosure relates to generally to additive manufacturing, and in particular to heat sinks for dissipating heat from objects being fabricated.

BACKGROUND

Additive manufacturing (AM) processes involve the buildup of one or more materials to make or form an object. AM encompasses various manufacturing and prototyping techniques known under a variety of names, including freeform fabrication, 3D printing, and rapid manufacturing/prototyping/tooling. AM techniques are capable of fabricating components having complex geometries from a wide variety of materials. Often, a freestanding object is fabricated using a computer-aided design (CAD) model. Certain types of AM processes use an energy beam, for example, an electron beam or electromagnetic radiation such as a laser beam, to sinter or melt a fine powder material, creating a solid three-dimensional object in which particles of the powder material are bonded together. Applications include direct manufacturing of complex workpieces, patterns for investment casting, metal molds for injection molding and die casting, and molds and cores for sand casting.

Selective laser sintering (SLS), direct metal laser sintering (DMLS), selective laser melting (SLM), and electron beam melting (EBM) are all common AM processes that involve successively depositing and heating layers of powder material to fuse the powder material and thereby produce three-dimensional (3D) objects as described, for example, in U.S. Pat. Nos. 10,525,688 and 10,716,673, the disclosures of which are hereby incorporated by reference herein. After heat is applied to the powder to induce sintering or melting, the layers of powder and indeed the object once initially formed retains the applied heat for a period of time. Portions of the object that remain heated are often in a weaker state than they are once the heat has dissipated. Certain objects may be formed by applying the entirety of sequential layers directly on top of previous layers or a build, i.e., start plate in the case of a first layer, in which the respective build plate or previous layers fully support their immediately following layers. However, other objects desirably may be formed with a base layer or layers supported by the build plate and a free hanging portion of the object extending laterally from the base layer without support from the build plate or previous layers. As such, free hanging portions are more susceptible to deformation after heat is applied to form those portions. In such circumstances, powder bed fusion supports are often required to prevent such deformation. Such supports require additional post-processing methods to have them removed which can be costly and involve time-consuming additional steps. Alternatively, contactless heat sinks may be used to draw heat away from free hanging portions, but may not be feasible, particularly when the intended structure being formed via an AM process has a feature that interferes with a contactless support, or may not be a sufficiently effective tool alone to achieve dimensionally stable horizontal regions with little to no deflection.

Further developments in the art of additively manufacturing objects having free hanging portions are therefore desired for improving the efficacy of such objects relative to their intended forms.

BRIEF SUMMARY

In accordance with an aspect, a first layer of powder may be deposited on a substrate and selectively scanned with a high energy beam to sinter or melt the powder and then further layers of powder may be deposited and selectively scanned successively to form portions of an intended object and a heat sink. The heat sink may be positioned beneath the free-hanging portion such that the heat sink draws heat away from the free-hanging portion as the portion is scanned to more rapidly improve the integrity of the free-hanging portion relative to a free-hanging portion fabricated without the use of a heat sink, and thereby reduce or eliminate unwanted deflection. The heat sink may be supported by the build plate or a powder bed formed in the AM process so that the heat sink does not contact the structure. In this manner, a heat sink may be employed directly under a free-hanging portion of an object during the formation of that portion while being directly over another portion of that object that already has been formed. The process may further include scanning the powder at different portions of the structure, such as a peripheral portion of the free-hanging element, at varying energy densities to further reduce or eliminate risk of deflection.

In accordance with another aspect, an in-process structure may be fabricated by an additive manufacturing process to have an overhanging feature in which an interfering feature, e.g., a second overhanging feature may be fabricated directly underneath the overhanging feature. During the additive manufacturing process, powder may be deposited on a build plate and the powder may be scanned with a high energy beam so as to sinter or melt the portions of the powder and thereby begin forming a base of the in-process structure and the interfering feature. Successive layers of powder may then be deposited and scanned over the first layer of powder so as to sinter or melt portions of such portions of the powder and thereby to continue forming the base and the interfering feature. Further successive layers of powder may then be deposited and portions of such successive layers may be semi-sintered with the high energy beam above the interfering feature to form a support for a heat sink positioned above the interfering feature. The heat sink subsequently may be formed by depositing still further successive layers of powder and scanning portions of such successive layers with the high energy beam so as to sinter or melt such portions of the powder such that portions of the heat sink are surrounded by and thereby anchored by the powder bed. Still further successive layers of powder then may be deposited and portions of such successive layers may be scanned with the high energy beam so as to sinter or melt such portions and thereby form the overhanging feature above or adjacent to the heat sink without contacting the heat sink. As the overhanging feature is scanned, the contactless heat sink may be configured to absorb heat away from the overhanging feature to prevent deformation. A plurality of in-process structures having an interfering feature, an overhanging feature, and a contactless heat sink for the overhanging feature may be formed simultaneously in an organized array on the build plate.

According to another aspect, an additively manufactured in-process combination may include a base, a first cantilever element extending from the base, and a first heat sink. The first heat sink may be adjacent to the first cantilever element and may be configured for absorbing heat from the first cantilever element during an additive manufacturing process. There may be a gap between the first heat sink and the first cantilever element, and the first heat sink may be spaced, e.g., by powder, from any rigid substrate, e.g., a build plate, underlying the first heat sink.

In some arrangements according to any of the foregoing, a portion of the first cantilever element may overlie a build plate of an additive manufacturing machine in which the additively manufactured in-process combination is being formed while not overlying the base.

In some arrangements according to any of the foregoing, the in-process combination may further include a powder bed. In such arrangements, the first heat sink may be supported by a support structure anchored in the powder bed. In some such arrangements, the support structure may have a width smaller than a width of the first heat sink. In some arrangements, the first heat sink may be supported by a plurality of support structures in which each of the support structures may have a width smaller than a width of the first heat sink. In some arrangements according to any of the foregoing, the powder bed may be disposed beneath the first heat sink and may be disposed directly beneath and support the support structure.

In some arrangements according to any of the foregoing, the powder bed may be disposed underneath an entirety of the first heat sink.

In some arrangements according to any of the foregoing, the base may include a base surface and the first cantilever element may extend in an orthogonal direction from the base surface.

In some arrangements according to any of the foregoing, the base may include a base surface and the first cantilever element may extend from the base surface.

In some arrangements according to any of the foregoing, the first heat sink may include a face proximate to and extend parallel to the first cantilever element, and the face of the first heat sink may be spaced from the first cantilever element.

In some arrangements according to any of the foregoing, the in-process structure may be an in-process femoral implant. In such an arrangement, at least a portion of the base may correspond to a condyle of the implant, and the first cantilever element may correspond to a peg of the implant.

In some arrangements according to any of the foregoing, the first heat sink may extend along a length of the first cantilever element.

In some arrangements according to any of the foregoing, the first heat sink may include a face having a profile in the same shape as a profile of the first cantilever element.

In some arrangements according to any of the foregoing, the in-process component may further include a second cantilever element and a second heat sink. In such an arrangement, the second heat sink may be configured for placement adjacent to the second cantilever element and may absorb heat from the second cantilever element during the additive manufacturing process. The base may include a main body, and the second cantilever element may extend from the main body in a direction parallel to the first cantilever element. The second heat sink may be spaced from the second cantilever element.

In some arrangements according to the foregoing, the second cantilever element and the second heat sink may be positioned above the first cantilever element and the first heat sink such that the first cantilever element, the first heat sink, the second cantilever element, and the second heat sink are positioned along the same axis.

In some arrangements according to the foregoing, the second cantilever element and the second heat sink may be positioned above the first cantilever element and the first heat sink such that the first heat sink and the second heat sink extend longitudinally along the same axis.

In some arrangements according to any of the foregoing, an additive manufacturing system of the in-process combination may include the in-process combination according to the foregoing and an additive manufacturing machine having a build plate. In such an arrangement, the second heat sink may be attached to the build plate.

In some arrangements according to any of the foregoing, the first cantilever element and the first heat sink may be made of the same material.

In some arrangements according to any of the foregoing, the first heat sink may include supports made from semi-sintered powder.

According to another aspect, a three-dimensional structure may be produced by a method of manufacturing. In this method, a first layer of powder may be deposited onto a substrate. The first layer may be selectively heated or scanned and thereby selectively heated, e.g., by sintering or melting, with a high energy beam to form a portion of a base of the structure. A first set of successive layers of the powder may be deposited onto the scanned first layer. At least a portion of the first set of successive layers of the powder may be selectively partially sintered or otherwise heated by the high energy beam to form an at least partially sintered or otherwise heated portion of a powder bed. At least a portion of each of the layers of the first set of successive layers of the powder may be selectively heated or scanned and thereby selectively heated, e.g., by sintering or melting, with the high energy beam to form additional portions of the base and a first heat sink spaced from the substrate. A second set of successive layers of the powder may be deposited onto the scanned first set of successive layers. Each of the layers of the second set of successive layers of the powder may be selectively heated or scanned and thereby selectively heated, e.g., by sintering or melting, with the high energy beam to form additional portions of the base and a cantilever element. The cantilever element may be directly attached to and may extend from the base. The cantilever element may be spaced from the heat sink.

In some arrangements according to any of the foregoing, the at least partially sintered or otherwise heated portion of the powder bed may be heated to a temperature less than a temperature to which the sintered or melted portions of the layers of powder are heated.

In some arrangements according to any of the foregoing, in the step of scanning each of the layers of the second set of successive layers, first portions of a first subset of the layers of the second set of successive layers of the powder corresponding to an edge of the cantilever element may be scanned with the high energy beam set at a first energy level. Further in the step of scanning each of the layers of the second set of successive layers, second portions of the first subset of the layers of the second set of successive layers of the powder corresponding to inner portions of the cantilever element spaced inwardly from the edge may be scanned with the high energy beam at a second energy level. The second energy level may be different from the first energy level.

In some arrangements according to any of the foregoing, the second energy level may be higher than the first energy level.

In some arrangements according to any of the foregoing, the step of scanning the first portions of the first subset of the layers of the second set of successive layers of the powder at the first energy level may be performed at a first scan speed. The step of scanning the second portions of the first subset of the layers of the second set of successive layers of the powder at the second energy level may be performed at a second scan speed. The second scan speed may be different from the first second speed.

In some arrangements according to any of the foregoing, the step of scanning the first portions of the first subset of layers of the second set of successive layers of the powder at the first energy level may be performed at a first current. The step of scanning the second portions of the first subset of the layers of the second set of successive layers of the powder at the second energy level may be performed at a second current. The second current may be different from the first current.

In some arrangements according to any of the foregoing, the cantilever element may be formed extending from the base in a direction transverse to a longitudinal axis defined by the base. In some arrangements according to any of the foregoing, the cantilever element may be formed extending from the base in a direction orthogonal to a longitudinal axis defined by the base. Each of the first portions of the first subset of the layers of the second set of successive layers of the powder may have a thickness between 1.2 millimeters and 1.8 millimeters.

In some arrangements according to any of the foregoing, the first energy level may supply an energy density of 2 J/mm². In some such arrangements, the second energy level may supply an energy density of 4 J/mm².

In some arrangements according to any of the foregoing, scanning the first layer may also form a portion of a base of a second structure. Scanning each of the layers of the first set of successive layers may also form additional portions of the base of the second structure, a second support structure anchored to the powder bed, and a second heat sink attached to the second support structure. Scanning each of the layers of the second set of successive layers may form additional portions of the second base and a second cantilever element. In such an arrangement, the second cantilever element may be directly attached to and extend from the second base. The second cantilever element may be spaced from the second heat sink.

In some arrangements according to any of the foregoing, the structure may form a first femoral component, in which the cantilever element may correspond to a first peg. The second structure may form a second femoral component, in which the second cantilever element may correspond to a second peg. The first and second femoral components may be formed to fit within each other with the peg of the first femoral component pointing toward the second femoral component, and the peg of the second femoral component pointing toward the first femoral component.

In some arrangements according to any of the foregoing, the powder may be a metallic powder.

According to another aspect, an additively manufactured in-process combination may include a powder, a base within the powder, a first cantilever element within the powder bed and extending from the base, and a first heat sink within the powder bed and adjacent to the first cantilever element, the first heat sink being configured for absorbing heat from the first cantilever element during an additive manufacturing process. In such embodiments, the first heat sink may be in contact with only the powder bed.

DETAILED DESCRIPTION

As used herein, the terms "about," "generally," "approximately," and "substantially" are intended to mean that slight deviations from absolute are included within the scope of the term so modified. However, unless otherwise indicated, the lack of any such terms should not be understood to mean that such slight deviations from absolute are not included within the scope of the term so modified.

The present disclosure describes a manufacturing process of a structure, using a medical implant as an example and in particular a femoral component, which is formed using a method of additive manufacturing (AM). It should be understood that the disclosed process is not limited to the fabrication of medical implants and may be used for other types of additively manufactured objects, such as those with cantilevered features. It should also be noted that reference to an in-process combination herein may refer to a structure formed during and/or after the AM process.

In some arrangements, one or more objects are fabricated by additive manufacturing means, such as by an SLS, SLM, or EBM process. The materials used to form the one or more objects may be, but are not limited to being, metal powder. Such metal powder may be, in some arrangements, any one or any combination titanium, titanium alloys such as but not limited to Ti-6Al-4V, stainless steel, cobalt chrome alloys, silver, tantalum and niobium.

The one or more objects include a base formed in a plurality of layers. A first layer of the base is formed on a substrate by depositing and then selectively scanning with a high energy beam, e.g., a laser or electron beam, a first layer of powder to sinter or melt and thereby fuse selective portions of the first layer of powder together. Successive layers of the powder are then deposited and selectively scanned with the high energy beam, layer by layer, to sinter or melt and thereby fuse selective portions of each of the successive layers of powder together over the first layer to form the base. During this process, each layer of the base being formed is supported by one or both of the substrate and the previously scanned layers as the powder is heated to be fused together, and the formed portions of the base have continued support while cooling.

Figure 1:
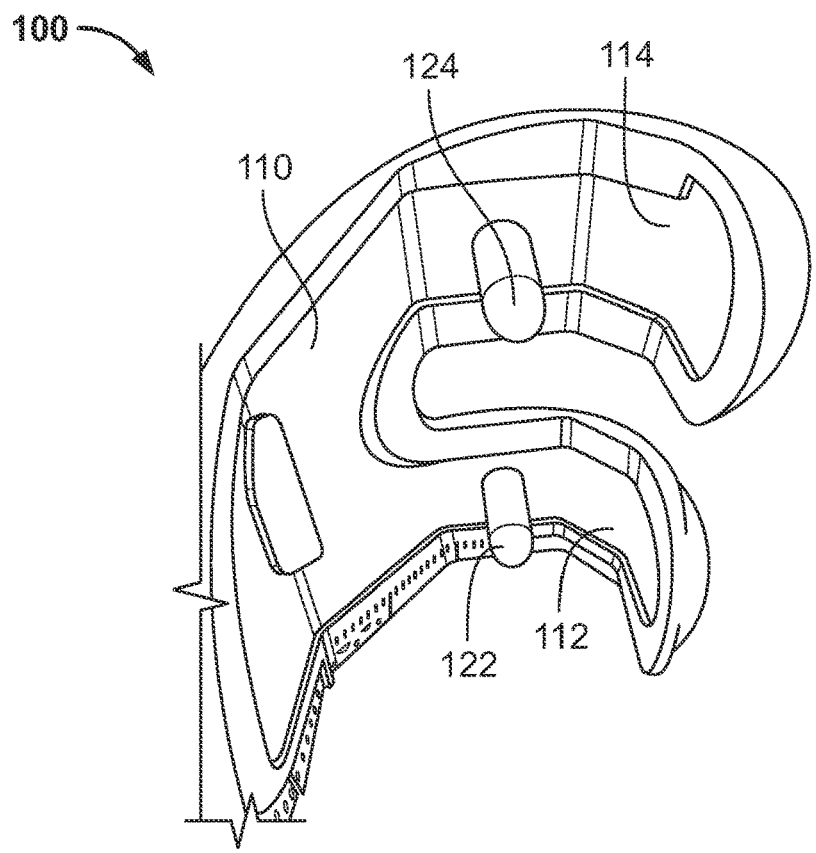
FIG. 1 is a perspective front view of an additively manufactured medical implant according to an embodiment.
Figure 2:
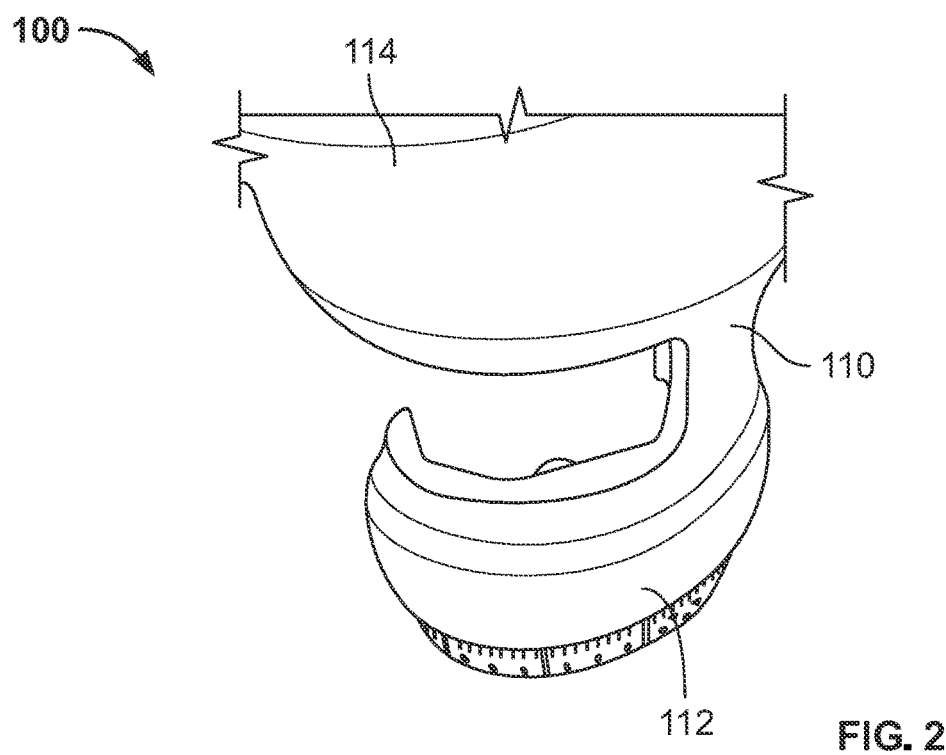
FIG. 2 is a perspective rear view of the medical implant of FIG. 1.

For example, as shown in FIGS. 1-2, the additively manufactured object may be femoral component 100 having flange 110, lower condyle 112, and upper condyle 114 as the base of the object. It should be noted that the terms "upper" and "lower" are used herein for ease of description to refer to elements of femoral component 100 as shown in the illustrated orientation, but the femoral component is not limited to such an orientation. As shown, femoral component 100 is oriented on its side, with a lower edge (i.e., an outer edge of flange 110 and lower condyle 112) adjacent the surface (not shown) on which the component lies. Lower condyle 112 and upper condyle 114 extend from flange 110 generally parallel to one another, with the upper condyle positioned directly above the lower condyle. Thus, in forming femoral component 100, a first layer of metal powder was deposited on a build plate of the manufacturing machine and that first layer of powder was selectively scanned by an electron beam, in this example, to form the lower edge of the femoral component and thus lower portions of lower condyle 112 and flange 110 nearest the build plate, which supported subsequent build layers as they were formed directly on top of the initial layer. It is contemplated that femoral component 100 may be formed in any orientation, such as having the opposing side of the femoral component (i.e., the outer edge of upper condyle 114 and the coextensive edge of flange 110) facing downward and abutting the build plate, resulting in the femoral component being formed in an orientation rotated 180 degrees from that shown in FIGS. 1 and 2.

The base of the structure may further include a cantilever element extending from the base and having a free end overhanging the build plate upon complete fabrication of the structure and removal of loose powder from the build plate. For example, femoral component 100 as shown in FIG. 1 includes lower peg 122 extending from a face of lower condyle 112 and acting as a cantilever element. Upper condyle 114 includes upper peg 124 extending from a face of the upper condyle and generally parallel to lower peg 122 in which the upper peg also acts as a cantilever element. Upper peg 124 and lower peg 122 lack material for support directly thereunder, and thus may have a risk of deformation while being formed. It should be understood that upper condyle 114 may also be considered a cantilever element because the upper condyle extends from flange 110 without being supported by any material directly beneath the upper condyle. However, upper condyle 114 in the illustrated example may have dimensions which include sufficient bulk material to act as its own heat sink, and it may be sufficient to form portions of the upper condyle with low energy density regions (as discussed further below) to prevent deformation. In FIGS. 1 and 2 femoral component 100 is shown after the AM process is complete.

Figure 3:
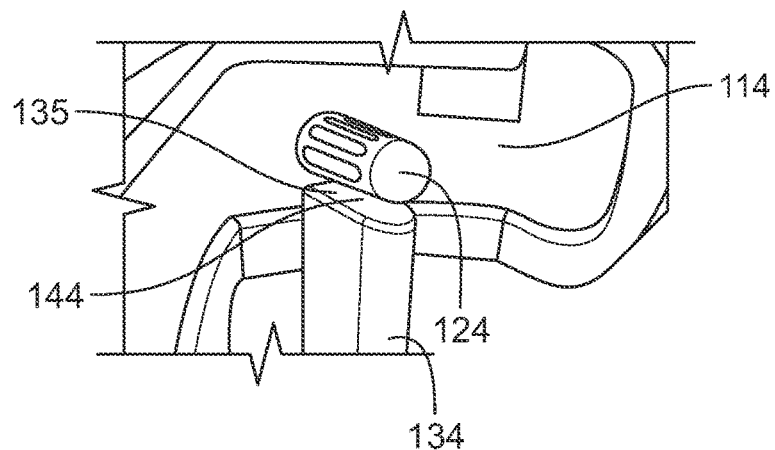
FIGS. 3-5 are perspective front views of an in-process medical implant and associated heat sink used in the formation of the medical implant of FIG. 1.
Figure 4:
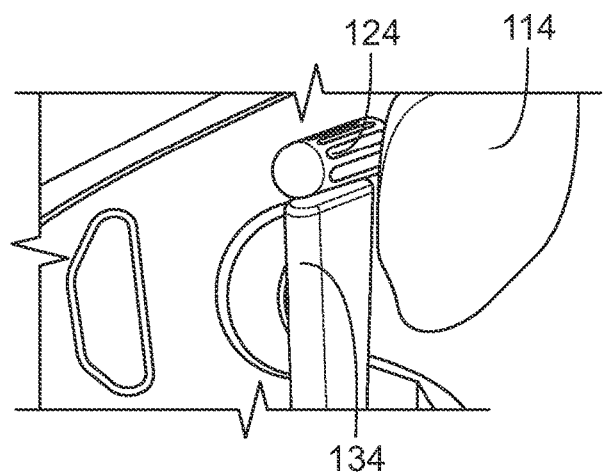
Figure 5:
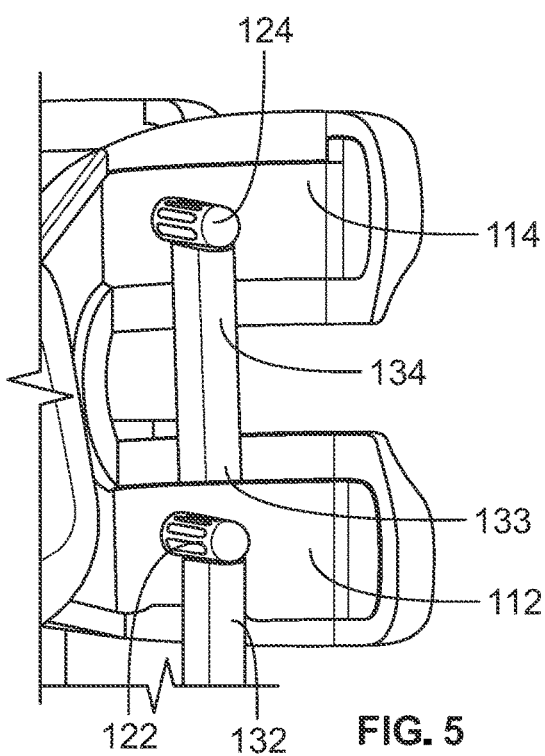

As demonstrated by FIGS. 3-5, at least one heat sink may be formed proximate to at least a portion of an object without contacting the femoral component such that the heat sink absorbs or draws heat away from the proximate portion of the object. In the example shown, upper heat sink 134 was formed along with femoral component 100 to absorb or draw heat away from upper peg 124 during and following fabrication of the upper peg. Upper heat sink 134 is formed by melting powder via the AM process before upper peg 124 such that the heat sink is fully formed as the powder is melted to form the upper peg. Upper heat sink 134 is sized and shaped with a length and width substantially the same as the length and width of upper peg 124 when the length and width of the upper peg are measured in directions parallel to a cross-sectional plane extending from upper condyle 114 and parallel to the substrate approximately through the center of the upper peg. In other words, the length of upper peg 124 is the distance from which the peg extends from upper condyle 114, and the width of the upper peg is the distance the peg extends along the upper condyle in a direction orthogonal to the length. Upper heat sink 134 is sized and shaped to absorb a sufficient amount of heat from upper peg 124 to solidify the structure of the upper peg in the desired shape in less time after being scanned by the high energy beam than without such heat sink, thereby reducing or preventing deformation of the upper peg due to the lack of material located directly below the upper peg for support. Upper heat sink 134 may have a height between about 3 mm and about 20 mm where height is measured in a directional orthogonal to the length and width dimensions and may be formed of the same or a different material than upper peg 124.

Upper heat sink 134 may be formed without contacting any portion of femoral component 100. As shown in FIGS. 3-5, upper heat sink 134 includes an upper surface 135 which faces toward and nearly abuts upper peg 124 in which the face is proximate to and extends along a plane generally parallel to the upper peg. There is a gap 144 of space left between upper heat sink 134 and upper peg 124, which, in some arrangements may measure between about 0.1 mm and about 0.6 mm but which varies for different features of various objects being fabricated based on factors including the thermal conductivity of the powder, the angle at which upper peg 124 extends from upper condyle 114, the amount of solid material contacting the upper peg (e.g., along the upper condyle) to absorb heat from the upper peg, and the thickness of the upper peg formed by the high energy beam with a relatively low energy density as described further below. Upper heat sink 134 has a generally vertical orientation such that the heat sink is positioned nearest a lower portion of upper peg 124. As shown in FIGS. 1 and 5, upper peg 124 is positioned directly above lower peg 122 in the illustrated orientation of femoral component 100, but as shown in the in-process example of FIG. 5 supports 133 for upper heat sink 134 may not contact the lower peg. Instead, as in this example, upper heat sink 134 may be formed to float in a powder bed such that the powder bed maintains the positioning and alignment of the upper heat sink relative to upper peg 124. In other words, the AM process (e.g., EBM process) may semi- or otherwise partially sinter powder to form a set of supports 133 as part of upper heat sink 134, which may be in the form of a "cake," by which the upper heat sink is anchored into the powder bed to position the heat sink in the desired location without contacting any surface of femoral component 100. It should be noted that loose or more preferably semi-sintered or at least partially sintered powder is contemplated as the support underneath upper heat sink 134.

The AM process of forming a femoral component 100 may further include a lower heat sink (lower heat sink 132 in the example of FIG. 5) configured to extract or draw heat away from lower peg 122. It should be noted that lower heat sink 132 may be substantially similar to upper heat sink 134 and may include any of the qualities and be supported in the same manner as described above with respect to the upper heat sink. As in the example shown, lower heat sink 132 may be substantially similar to upper heat sink 134, with the exception that the lower heat sink may be positioned below lower peg 122 and formed during the AM process extending from the substrate for support without contacting any surface of femoral component 100. That is, lower heat sink 132 may be formed in layers beginning at the substrate with the lower heat sink being oriented generally vertically and having a height such that the lower heat sink extends from the substrate to lower peg 122 without contacting the lower peg. In this manner, a gap is left between lower heat sink 132 and lower peg 122 similar to gap 144. Lower heat sink 132 may have a length and width substantially similar to the length and width of lower peg 122 when the dimensions of the lower peg are measured in directions parallel to a cross-sectional plane extending from lower condyle 112 and parallel to the substrate approximately through the center of the lower peg. Similar to upper peg 124, the length of lower peg 122 is the distance the lower peg extends from lower condyle 112, and the width of the lower peg is the distance along the first condyle the lower peg extends in the direction orthogonal to that of the length. Lower heat sink 132 is sized and shaped to absorb a sufficient amount of heat from lower peg 122 to solidify the structure of the lower peg in the desired shape as the lower peg is scanned with the high energy beam than without such heat sink, thereby reducing or preventing deformation of the lower peg. Lower heat sink 132 may be formed of the same or different materials than lower peg 122.

Figure 6:
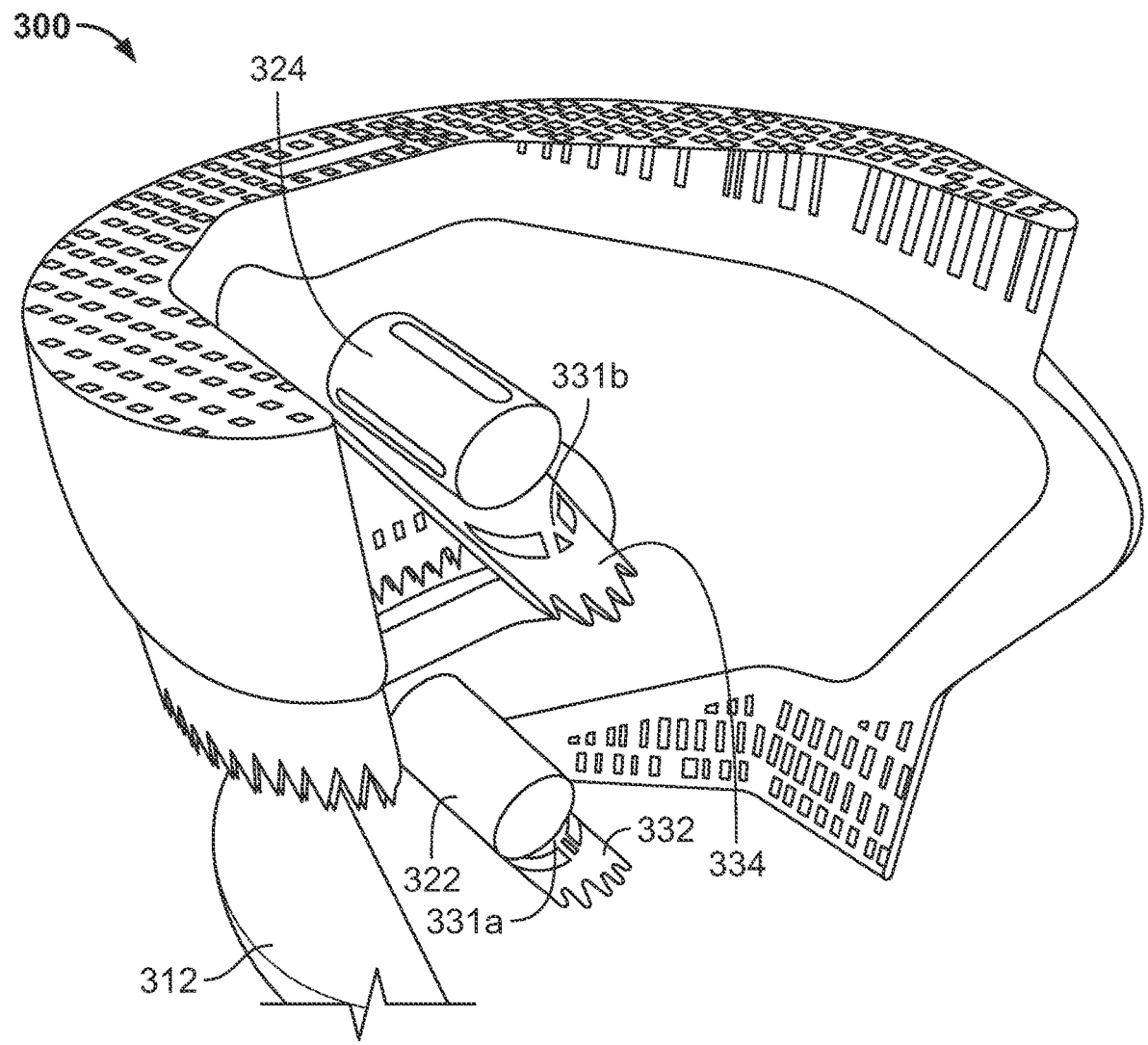
FIG. 6 is a perspective view of an in-process object according to another embodiment.

Referring now to FIG. 6, femoral component 300 is substantially similar to femoral component 100, with the exception of upper heat sink 334 and lower heat sink 332 having different orientations than upper heat sink 124 and lower heat sink 134. Lower heat sink 332 was formed below lower peg 322, but the lower heat sink is not supported by and does not contact the substrate upon which femoral component 300 sits. Instead, lower heat sink 332 extends generally along and parallel to lower peg 332, and is coupled to the lower peg by small struts 331a extending across a gap formed between the lower heat sink and the lower peg, such that the lower heat sink and the lower peg are contactless with the exception of the small struts. It is contemplated that lower heat sink 332 may contact lower condyle 312 for additional support. Upper heat sink 334 and upper peg 324 have the same or substantially the same configuration as lower heat sink 332 and lower peg 322. That is, upper heat sink 334 was formed generally along and parallel to upper peg 324, but does not contact the upper peg with the exception of struts 331b. Thus, upper heat sink 334 is positioned adjacent to upper peg 324, without substantially contacting the upper peg, and is positioned directly above lower peg 322. In this manner, lower and upper heat sinks 332, 334 may require relatively less support from the powder bed than fully contactless arrangements like those used additively manufacturing femoral component 100.

In certain alternative examples, the heat sink may be sized and shaped to generally contour a surface of the cantilever element without contacting the cantilever element. For instance, as shown in FIG. 6, upper peg 324 is cylindrical, having a rounded surface, and upper heat sink 334 has a corresponding rounded surface proximate to the upper peg. Although upper heat sink 334 is attached to upper peg 324 in the example shown in FIG. 6, the configuration described in the present example may also apply to heat sinks which do not contact their respective cantilever elements and are, e.g., floating in a powder bed.

In some examples, a lower heat sink may be attached to the base structure rather than the substrate. For instance, instead of lower heat sink 132 extending downward relative to lower peg 122 as shown in FIG. 5 to be supported by the substrate or base plate, the lower heat sink may be coupled to lower condyle 112 for support. Such an example may be similar to that shown in FIG. 6, in the manner that lower heat sink 332 does not contact the substrate, but may instead be coupled to the base structure of the object, e.g., lower condyle 312. It is also contemplated that an upper heat sink may be attached to the base structure in a manner substantially similar to that described above with respect to the lower heat sink and lower condyle.

In further examples, the AM process may include formation of a plate-like feature which does not contact the object being fabricated but is merely supported by the powder bed above an interfering feature, e.g., lower peg 122. The plate-like feature may be attached to the heat sink and thereby act as a substrate for the heat sink in the powder. Such a feature may provide improved balance for the heat sink relative to anchoring the heat sink to the substrate or base object, which may ensure that the heat sink remains in the desired alignment with the cantilever element during manufacturing.

Figure 7:
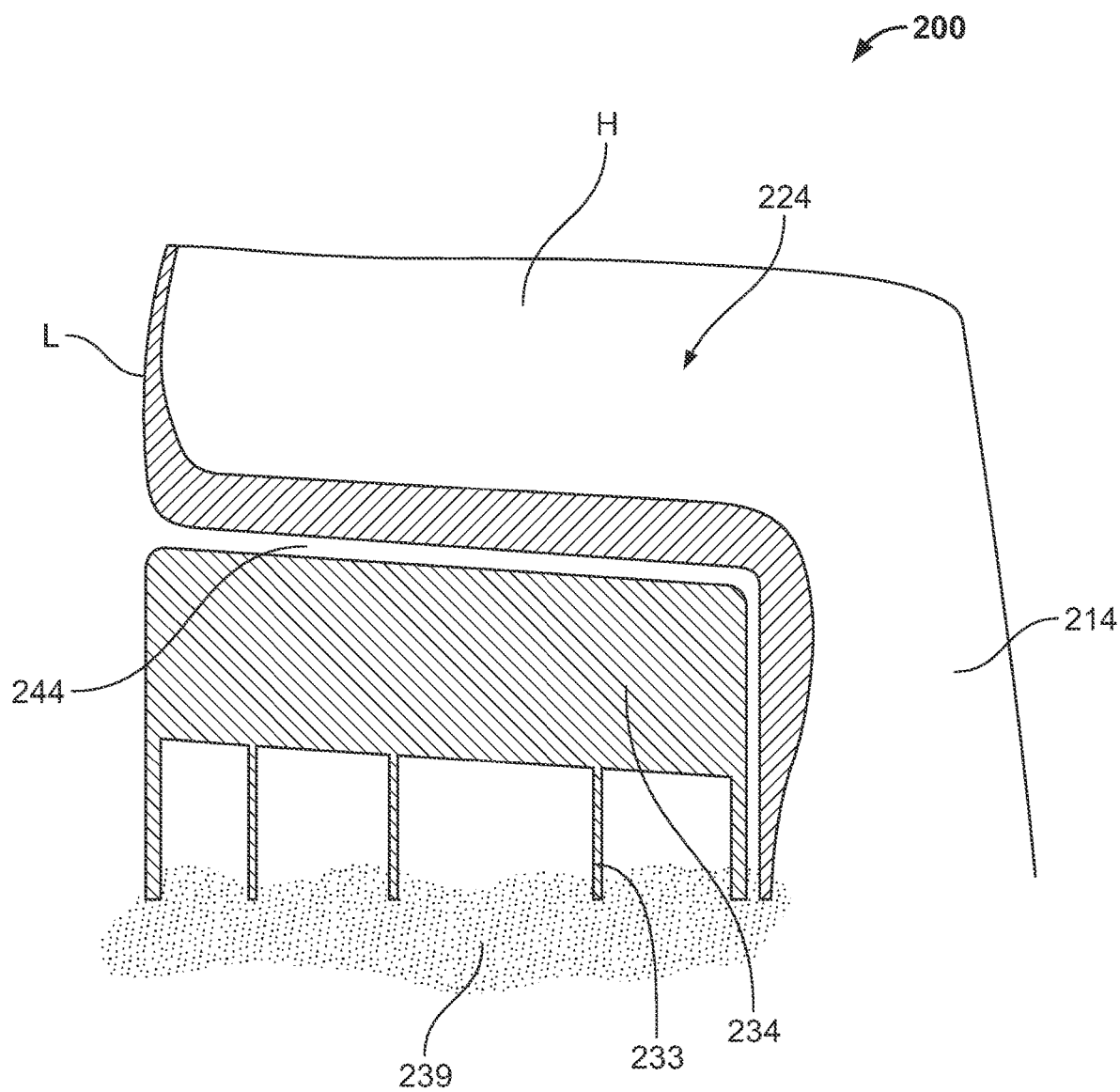
FIG. 7 is a schematic side view of an in-process object formed with a heat sink and illustrating the use of varying energy densities of a high energy beam over preselected regions of the object in accordance with an embodiment.

As shown in the schematic illustration of FIG. 7, object 200 includes base 214 and cantilever element 224 extending from the base in which the base and the cantilever element are spaced from heat sink 234. Such a configuration is similar to the relative placement of upper condyle 114 and upper peg 124 relative to upper heat sink 134 as described above. Heat sink 234 includes supports 233 which may be anchored into a semi- or otherwise partially sintered powder bed 239. Base 214 extends generally in an upward direction away from the substrate. Cantilever element 224 extends in a direction generally orthogonal to base 214, approximately forming a right angle between the cantilever element and the base. It is, however, contemplated that cantilever element 224 may extend from base 214 at any angle, as discussed further below. Cantilever element 224 and heat sink 234 are each formed separately without contacting each other, thereby defining a gap 244 therebetween. Due to the moment force that may occur by forming object 200 with cantilever element 224 extending from base 214 without support directly beneath the cantilever element, the cantilever element may be structurally formed in a manner which may further mitigate the risk of deformation of the cantilever element. That is, region H of cantilever element 224 may be formed by applying a high energy density, and region L of the cantilever element may be formed with a low energy density. High and low energy densities may be applied within regions H, L by modifying at least one variable of the high energy beam as the beam is directed onto and scans the powder. In some examples, the power and scan speed of the energy beam may be adjusted accordingly to provide for a higher or lower energy density. That is, the power may be relatively increased and scan speed may be relatively decreased in forming a region with a relatively high energy density, and alternatively, power may be relatively decreased and scan speed may be relatively increased in forming a region with a relatively low energy density. In some arrangements, the power of the energy beam may be changed by increasing or decreasing the current applied to the energy beam. In some examples, multispot melting may be applied to vary the energy density of cantilever element 224. That is, for a particular region or regions preferably on or near the surface of the component being manufactured, the EBM machine (or other AM machine, such as a laser-based machine) may use a sequence of small melt lines called "spots," and the beam may move rapidly from one spot to another in a different region such that multiple melt pools are actively melted nearly simultaneously. Multispot melting may be useful for forming a low energy density region of femoral component 100.

It is to be understood that an object may be formed by applying a high energy beam with relatively high and low energy densities across either one or both of various regions H, L and various elements of the object. Regions H may be subjected to a relatively high energy density of between and including about 3.5 J/mm$^2$ and about 4.5 J/mm$^2$, and preferably about 4 J/mm$^2$. Regions L may be subjected to a relatively ow energy density region between and including about 1.5 J/mm$^2$ and about 2.5 J/mm$^2$, and preferably about 2 J/mm$^2$.

Figure 8:
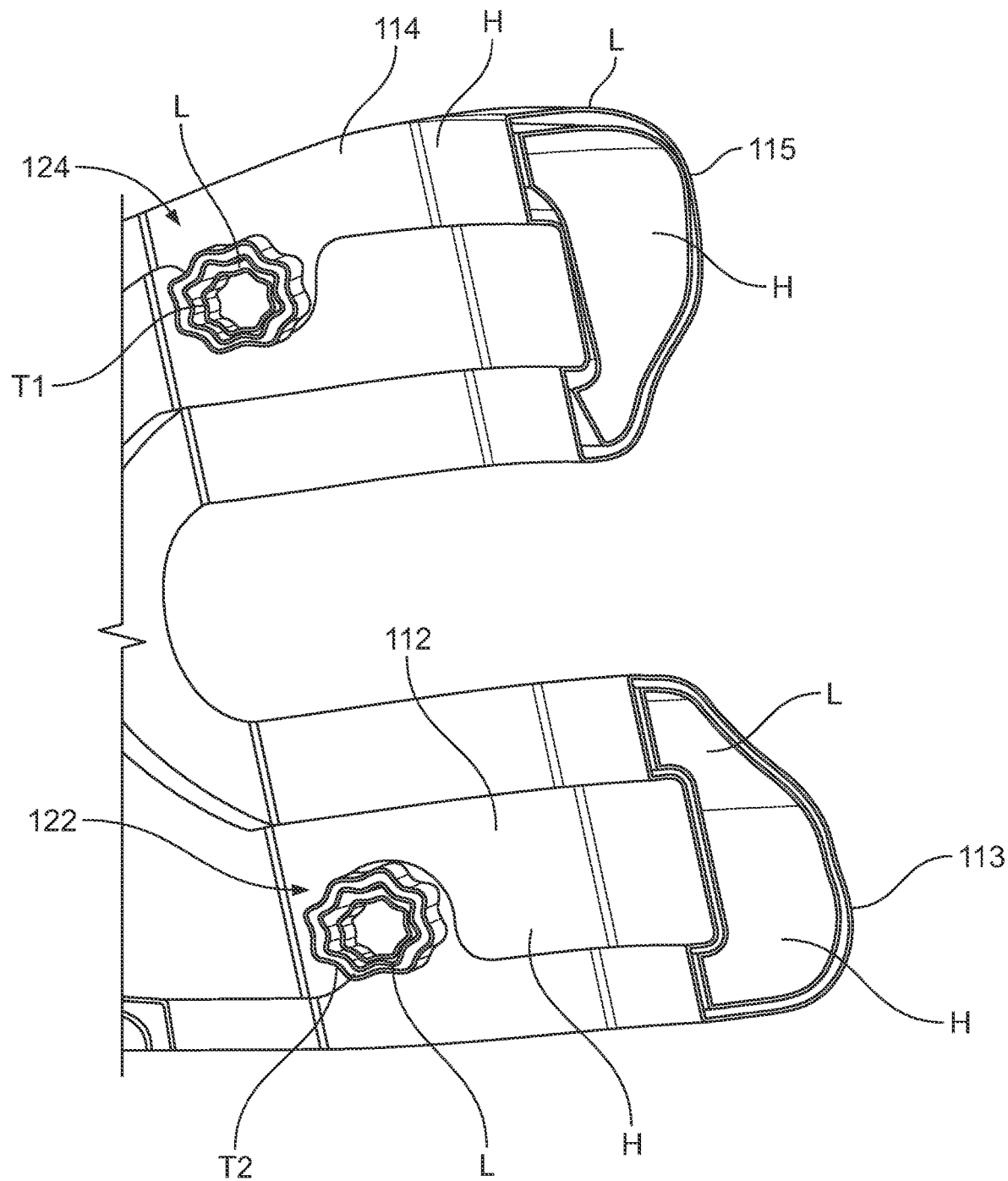
FIG. 8 is a schematic cross-sectional view of a medical implant illustrating the application of varying energy densities of a high energy beam over preselected regions of a medical implant in accordance with an embodiment.

Referring again to femoral component 100, as shown in FIG. 8, upper peg 124 includes a radially outer portion having a thickness T1 that extends around a circumference of the upper peg and that is a region L subjected to a relatively low energy density. Although the image shows upper peg 124 having a hollow interior portion, it is contemplated that the upper peg has a radially inner portion within the radially outer portion of upper peg 124 shown in which the radially inner portion is a region H subjected to a relatively high energy density. In the illustrated example, lower peg 122 includes generally the same structure as upper peg 124, but may have a different structure from the upper peg in other examples. Any combination of thickness T1 and T2 are contemplated for each of upper and lower pegs 124, 122.

It is contemplated that a cantilever element may extend from a base structure at any angle, and respective thicknesses T1 and T2 may vary based on the angle at which a cantilever element extends from a base structure. For instance, with respect to the example of FIG. 8, upper peg 124 may extend at an angle oblique to upper condyle 114, forming either an acute or obtuse angle between the upper peg and the upper condyle. When upper peg 124 extends generally horizontally, i.e., orthogonally, relative to upper condyle 114, region L of the upper peg subjected to a relatively low energy density may have a thickness T1 measuring between and including about 1.2 mm and about 1.8 mm. When upper peg 124 extends at an angle oblique to upper condyle 114, e.g., forming approximately a 60-degree angle between a plane defined by a surface of the upper condyle surrounding the upper peg and an axis defined by the upper peg, region L of the upper peg may have a thickness T1 measuring between and including about 0.2 mm and about 0.4 mm, and preferably about 0.3 mm. It is further contemplated that when upper peg 124 extends from upper condyle 114 forming an angle of less than 60 degrees between the plane defined by the surface of the upper condyle surrounding the upper peg and the axis defined by the upper peg, region L of the upper peg may have a thickness T1 between and including about 0.3 mm and 1.8 mm, and the variation of the thickness may be generally proportional to the variation of the angle. The variations of the angle of extension of upper peg 124 and corresponding thickness T1 for region L of upper peg 124 subjected to a relatively low energy density as described herein are also contemplated for the thickness of the radially outer portion of lower peg 122.

Further in the example shown in FIG. 8, upper condyle 114 having terminal end 115 and lower condyle 112 having terminal end 113 each have regions subjected to high and low energy densities near their respective terminal ends. Specifically, upper condyle 114 includes a region L subject to a low energy density by a high energy beam located above a region H subjected to a high energy density by such beam, and lower condyle 112 includes another region L located above another region H. Upper heat sink 134 (not shown in FIG. 8) and lower heat sink 132 (not shown in FIG. 8) may be formed as regions H subjected to a relatively high energy density or densities.

The method for additively manufacturing a three-dimensional object may be performed in a cycle. A cycle may begin with depositing a first layer of powder onto a substrate, which may be a start plate. The first layer of powder may be selectively scanned with a high energy beam such as a laser or electron beam to sinter or melt the first layer of powder and to form initial portions of both the base of the object, e.g., flange 110 and lower condyle 112, and supports for a heat sink, e.g., lower heat sink 132. After at least a first layer is scanned, successive layers of powder may be deposited and each such successive layer may be selectively scanned in a manner substantially similar to the first layer. The machine depositing the powder may be programmed to deposit the powder in locations corresponding to the shape of the three-dimensional object programmed into the machine (e.g., femoral component 100) and the accompanying heat sinks. Additional layers may be deposited and scanned to form a lower cantilever element extending from the base structure, such as lower peg 122, which is formed over lower heat sink 132 without contacting the lower heat sink. Lower heat sink 132 is configured to absorb heat from the lower cantilever element 122 as the powder is scanned to form the lower peg. After the lower cantilever element 122 is formed over lower heat sink 132, the machine eventually may begin formation of upper heat sink 134. To form a heat sink floating in a powder bed, such as upper heat sink 134 shown in FIG. 5, a portion of the deposited powder may be semi- or otherwise partially sintered to form a semi- or otherwise partially sintered powder bed. The semi- or otherwise partially sintered powder bed may form a floor positioned above lower cantilever element 122 to which supports 133 for upper heat sink 134 are anchored. It should be noted that while the powder may be partially sintered in one section of a layer, while being fully sintered or melted in another part of the same layer to simultaneously form a portion of femoral component 100. Once the powder bed is laid, subsequent layers of powder may be deposited thereon and scanned with the high energy beam to form additional portions of the base, e.g., flange 110 and condyles 112, 114, as well as support structure 133, and upper heat sink 134.

When upper heat sink 134 is formed, still further additional layers of powder may be deposited and scanned thereon to continue forming the base (such as upper condyle 114) and an upper cantilever element, e.g., upper peg 124, extending from the upper base. Upper cantilever element 124 is formed over upper heat sink 134 without contacting the upper heat sink. Upper heat sink 134 is configured to draw heat from upper cantilever element 124 as the powder forming the upper cantilever element is scanned. Additional layers may be deposited and scanned until the object 100 is fully formed, completing one full AM cycle. Upper cantilever element 124, upper base 114, lower cantilever element 122, and lower base 112 may each have regions H subjected to a high energy beam with a high energy density and regions L subjected to a high energy beam with a low energy density as described above and illustrated in FIG. 8. In such examples, the AM machine may be instructed appropriately, such as by programming scan speed and beam power settings corresponding to preselected L and H regions, to apply the high energy beam with a first energy density, such as 2 J/mm$^2$, while scanning the powder within one or more regions L, and to apply the high energy beam with a second energy density, such as 4 J/mm², while scanning the powder within one or more regions H. As noted above, implementing the above-described process may eliminate the need to form supports that directly contact the cantilever element while still retaining dimensional stability, material properties, surface finish, etc., even when such supports cannot be fabricated directly on a build plate of the AM machine.

Figure 9:
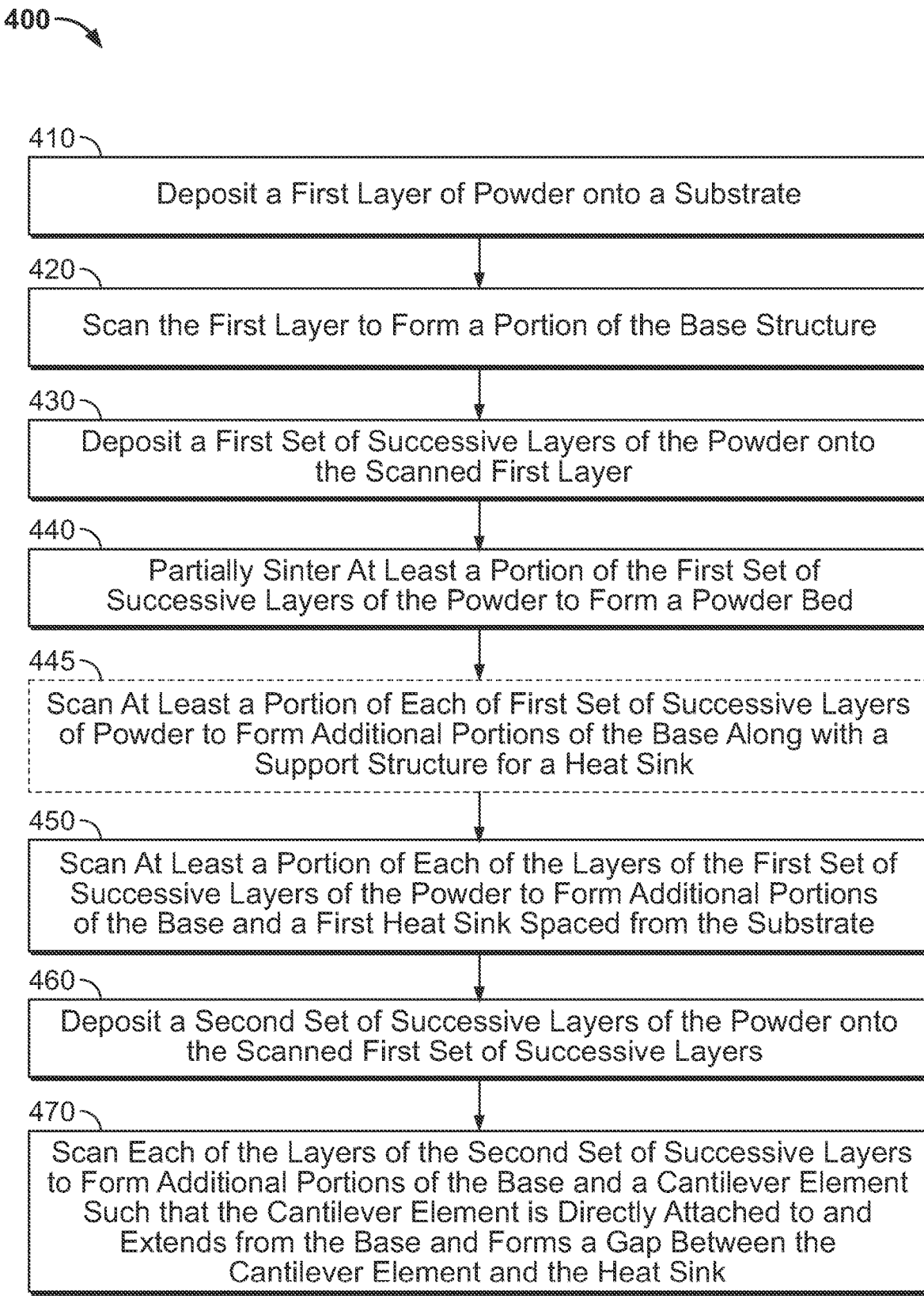
FIG. 9 is a process flow chart showing the steps of additively manufacturing an object according to an embodiment.

Referring now to FIG. 9, a three-dimensional structure is manufactured by a process 400. In process 400, a structure, such as femoral component 100, 300 or object 200, may be formed. At step 410, a first layer of powder is deposited onto a substrate. At step 420, the first layer of powder is scanned, e.g., by an AM machine, with a high energy beam to form a portion of the base structure. At step 430, a first set of successive layers of powder is deposited onto the scanned first layer. At step 440, at least a portion of the first set of successive layers of powder is semi- or otherwise partially sintered to form a semi- or otherwise partially sintered powder bed for directly supporting or for anchoring a support structure for supporting a heat sink. At optional step 445, at least a portion of the first set of successive layers of powder is scanned to form additional portions of the base along with a support structure or supports for the heat sink. At step 450, at least a portion of the layers of the first set of successive layers of powder is scanned to form additional portions of the base along with a heat sink spaced from the substrate. At step 460, a second set of successive layers of the powder is deposited onto the scanned first set of successive layers. At step 470, each of the layers of the second set of successive layers is scanned to form additional portions of the base and a cantilever element. In this manner, the cantilever element is directly attached to and extends from the base and a gap is formed between the cantilever element and the heat sink. In some arrangements the cantilever element is formed spaced from the heat sink, such as in the example of femoral component 100 as shown in FIGS. 3-5, while in some other arrangements a portion of the cantilever element is attached to the heat sink, such as in the example of femoral component 300 as shown in FIG. 6.

It is to be further understood that the disclosure set forth herein includes any possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the disclosure.

Although particular embodiments have been described herein, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An additively manufactured in-process combination, comprising:
 a powder bed;
 a base;
 a first cantilever element extending from the base, wherein a first region of the first cantilever element is formed with a first energy density and a second region of the first cantilever element is formed with a second energy density greater than the first energy density;
 a first heat sink adjacent to the first cantilever element and configured for absorbing heat from the first cantilever element during an additive manufacturing process,
 wherein there is a gap between the first cantilever element and the first heat sink and the first heat sink is in contact with only the powder bed, and
 wherein the gap is directly bounded by the first heat sink and the first region of the first cantilever element.

2. The in-process combination of claim 1, wherein the first heat sink is supported by a support structure anchored in the powder bed, the support structure having a width smaller than a width of the first heat sink.

3. The in-process combination of claim 2, wherein the powder bed is directly beneath the first heat sink.

4. The in-process combination of claim 1, wherein the base includes a base surface and the first cantilever element extends from the base surface.

5. The in-process combination of claim 1, wherein the first heat sink includes a face proximate to and extending parallel to the first cantilever element, and the face of the heat sink is spaced from the first cantilever element.

6. The in-process combination of claim 1, wherein the in-process combination is an in-process femoral implant, at least a portion of the base corresponds to a condyle of the implant, and the first cantilever element corresponds to a peg of the implant.

7. The in-process combination of claim 1, wherein the first heat sink includes a face having a profile in the same shape as a profile of the first cantilever element.

8. The in-process combination of claim 1, further comprising:
 a second cantilever element; and
 a second heat sink configured for placement adjacent the second cantilever element and absorbing heat from the second cantilever element during the additive manufacturing process, wherein the base includes a main body and the second cantilever element extends from the main body in a direction parallel to the first cantilever element, and wherein the second heat sink is spaced from the second cantilever element.

9. The in-process combination of claim 8, wherein the second cantilever element and the second heat sink are positioned above the first cantilever element and the first heat sink such that the first cantilever element, the first heat sink, the second cantilever element, and the second heat sink are positioned along the same axis.

10. An additive manufacturing system, comprising:
 the in-process combination of claim 8; and
 an additive manufacturing machine including a build plate,
 wherein the second heat sink is attached to the build plate.

11. The in-process combination of claim 1, wherein the first heat sink includes supports made of semi-sintered powder.

12. A method of manufacturing a three-dimensional structure comprising the steps of:
 depositing a first layer of powder onto a substrate;
 selectively heating the first layer with a high energy beam to form a portion of a base of the structure;
 depositing a first set of successive layers of the powder onto the heated first layer,
 selectively at least partially sintering at least a portion of the first set of successive layers of the powder to form an at least partially sintered portion of a powder bed;
 selectively heating at least a portion of each of the layers of the first set of successive layers of the powder with the high energy beam to form additional portions of the base and a first heat sink spaced from the substrate, wherein the first heat sink does not contact the substrate;

depositing a second set of successive layers of the powder onto the heated first set of successive layers, selectively heating layers of the second set of successive layers of the powder with the high energy beam to form additional portions of the base and a first region of a cantilever element at a first energy density, and selectively heating layers of the second set of successive layers of the powder with the high energy beam to form a second region of the cantilever element at a second energy density different from the first energy density such that the cantilever element is directly attached to and extends from the base and the second region of the cantilever element is facing and spaced from the heat sink.

13. The method of claim 12, wherein the step of selectively heating the layers of the second set of successive layers includes selectively heating i) first portions of a first subset of the layers of the second set of successive layers of the powder corresponding to an edge of the cantilever element with the high energy beam set at a first energy level and ii) second portions of the first subset of the layers of the second set of successive layers of the powder corresponding to inner portions of the cantilever element spaced inwardly from the edge with the high energy beam at a second energy level different from the first energy level.

14. The method of claim 13, wherein the step of selectively heating the first portions of the first subset of the layers of the second set of successive layers of the powder at the first energy level is performed at a first scan speed, and wherein the step of scanning the second portions of the first subset of the layers of the second set of successive layers of the powder at the second energy level is performed at a second scan speed different from the first scan speed.

15. The method of claim 13, wherein the step of scanning the first portions of the first subset of the layers of the second set of successive layers of the powder at the first energy level is performed at a first current, and wherein the step of scanning the second portions of the first subset of the layers of the second set of successive layers of the powder at the second energy level is performed at a second current different from the first current.

16. The method of claim 13, wherein the cantilever element is formed extending from the base in a direction transverse to a longitudinal axis defined by the base, and wherein each of the first portions of the first subset of the layers of the second set of successive layers of the powder has a thickness between 1.2 and 1.8 millimeters.

17. The method of claim 13, wherein the first energy level supplies an energy density of 2 J/mm$^2$ and the second energy level supplies an energy density of 4 J/mm$^2$.

18. The method of claim 12, wherein the step of selectively heating the first layer also forms a portion of a base of a second structure, the step of selectively heating each of the layers of the first set of successive layers also forms additional portions of the base of the second structure, a second support structure anchored to the powder bed, and a second heat sink attached to the second support structure, and the step of heating each of the layers of the second set of successive layers forms additional portions of the second base and a second cantilever element such that the second cantilever element is directly attached to and extends from the second base and is spaced from the second heat sink.

19. An additively manufactured in-process combination, comprising:
a powder bed supported by a substrate;
a base within the powder bed;
a first cantilever element within the powder bed and extending from the base, the first cantilever element including a first region formed with a first energy density and a second region formed with a second energy density greater than the first energy density;
a first heat sink within the powder bed, the first heat sink being spaced apart from the substrate by the powder bed, and the first heat sink being configured for absorbing heat from the first region of the first cantilever element during an additive manufacturing process,
wherein the first heat sink is in contact with only the powder bed.

20. The additively manufactured in-process combination of claim 1, wherein the second region of the first cantilever element is separated from the heat sink by the first region of the first cantilever element.

* * * * *